United States Patent
Holroyd et al.

(10) Patent No.: US 11,801,158 B2
(45) Date of Patent: Oct. 31, 2023

(54) OSTOMY APPLIANCE COUPLING ASSEMBLY

(71) Applicant: ConvaTec Limited, Flintshire (GB)

(72) Inventors: Simon Holroyd, London (GB); Dominic Baker, London (GB); Stefan Taal, London (GB)

(73) Assignee: ConvaTec Limited, Flintshire (GB)

( * ) Notice: Subject to any disclaimer, the term of this patent is extended or adjusted under 35 U.S.C. 154(b) by 0 days.

(21) Appl. No.: 17/883,949

(22) Filed: Aug. 9, 2022

(65) Prior Publication Data

US 2022/0401250 A1    Dec. 22, 2022

Related U.S. Application Data

(63) Continuation of application No. PCT/GB2021/050408, filed on Feb. 19, 2021.

(30) Foreign Application Priority Data

Feb. 20, 2020 (GB) ..................... 2002393

(51) Int. Cl.
*A61F 5/445* (2006.01)
*A61F 5/44* (2006.01)
*A61F 5/448* (2006.01)

(52) U.S. Cl.
CPC ............ *A61F 5/445* (2013.01); *A61F 5/4404* (2013.01); *A61F 2005/4486* (2013.01)

(58) Field of Classification Search
CPC . A61F 5/445; A61F 5/4404; A61F 2005/4486
See application file for complete search history.

(56) References Cited

U.S. PATENT DOCUMENTS

| | | | | |
|---|---|---|---|---|
| 2,796,063 A | * | 6/1957 | Smelser ................. | A61F 5/448 604/342 |
| 3,042,430 A | * | 7/1962 | Guy ........................ | F16L 23/06 24/270 |

(Continued)

FOREIGN PATENT DOCUMENTS

| | | | | |
|---|---|---|---|---|
| EP | 680736 A1 | | 8/1995 | |
| EP | 1894454 A1 | * | 3/2008 | ............. B81B 7/007 |

(Continued)

OTHER PUBLICATIONS

Written Opinion of International Searching Authority for International Application No. PCT/GB2021/050408; dated Apr. 29, 2021; 6 pages.

(Continued)

*Primary Examiner* — Guy K Townsend
(74) *Attorney, Agent, or Firm* — Taft Stettinius & Hollister LLP; Ryan O. White; Derek B. Lavender

(57) ABSTRACT

The present disclosure provides a coupling assembly (12) for an ostomy appliance (10) comprising a clamp arrangement (60), a first coupling and a second coupling. The clamp arrangement (60) comprises a clamp ring (61) mounted to the first and/or second coupling and a clamp locked mounted to the clamp ring (61). The clamp ring (61) comprises an inner circumference (62) adjustable between clamped and unclamped configurations. In the clamped configuration the clamp ring (61) is for maintaining the first and second couplings (20, 40) in a coupled configuration. The clamp lock (80) is adjustable into a locked configuration to lock the clamp ring (61) in the clamped configuration. The clamp lock (80) comprises a clamp actuator (81) moveable radially relative to the inner circumference (62) to unlock the clamp lock (80) from the locked configuration.

17 Claims, 5 Drawing Sheets

(56) References Cited

U.S. PATENT DOCUMENTS

| | | | | |
|---|---|---|---|---|
| 3,276,089 A * | 10/1966 | Cheever | F16L 33/12 24/270 |
| 4,438,958 A * | 3/1984 | De Cenzo | F16L 21/06 439/100 |
| 4,850,985 A * | 7/1989 | Edwards | A61F 5/448 604/339 |
| 4,917,691 A * | 4/1990 | Briggs | A61F 5/448 604/339 |
| 4,963,136 A * | 10/1990 | Steer | A61F 5/448 604/339 |
| 5,026,360 A * | 6/1991 | Johnsen | A61F 5/448 604/338 |
| 5,180,377 A * | 1/1993 | Holtermann | B65D 45/345 604/338 |
| 5,322,523 A * | 6/1994 | Olsen | A61F 5/448 604/338 |
| 5,364,379 A * | 11/1994 | Ozenne | F16L 37/008 604/344 |
| 5,496,297 A * | 3/1996 | Olsen | A61F 5/448 604/338 |
| 5,647,861 A * | 7/1997 | Steer | C07C 43/11 604/338 |
| 5,843,053 A * | 12/1998 | Steer | A61F 5/448 604/338 |
| 5,902,295 A * | 5/1999 | Steer | A61F 5/448 604/338 |
| 5,957,905 A * | 9/1999 | Steer | A61F 5/448 604/338 |
| 8,870,742 B2 * | 10/2014 | Dlugos, Jr. | A61B 5/0022 600/37 |
| 8,985,647 B2 * | 3/2015 | Kuzelka | B65D 45/345 292/256.65 |
| 9,345,612 B2 * | 5/2016 | Hanuka | A61F 5/448 |
| 9,669,969 B2 * | 6/2017 | Taylor | B65D 21/0219 |
| D796,029 S * | 8/2017 | Hanuka | A61F 5/448 D24/118 |
| 10,010,443 B2 * | 7/2018 | Becker | A61F 5/448 |
| 10,034,792 B2 * | 7/2018 | Pedersen | A61F 5/448 |
| 2002/0165507 A1 * | 11/2002 | Hessel | A61F 5/448 604/342 |
| 2009/0118687 A1 * | 5/2009 | Kristensen | A61F 5/448 604/342 |
| 2014/0324003 A1 * | 10/2014 | Becker | A61F 5/448 604/342 |
| 2015/0045755 A1 * | 2/2015 | Pedersen | A61F 5/448 604/342 |
| 2021/0259875 A1 * | 8/2021 | Holroyd | A61F 5/448 |

FOREIGN PATENT DOCUMENTS

| | | | | |
|---|---|---|---|---|
| EP | 1894547 A1 * | 3/2008 | | A61F 5/448 |
| EP | 1894547 A1 | 3/2008 | | |
| WO | 9101118 A1 | 2/1991 | | |
| WO | WO-199101118 A1 * | 2/1991 | | A61F 5/44 |

OTHER PUBLICATIONS

Request for Preliminary Examination of International Application No. PCT/GB2021/050408; dated Dec. 17, 2021; 10 pages.

International Preliminary Report on Patentability; dated Apr. 13, 2022; 6 pages.

* cited by examiner

OSTOMY APPLIANCE COUPLING ASSEMBLY

TECHNICAL FIELD

The present disclosure relates to a coupling assembly for an ostomy appliance and an ostomy appliance comprising such a coupling assembly.

BACKGROUND OF THE DISCLOSURE

There are many forms of ostomy appliances which aim to provide a secure, comfortable fit for ostomates. Ostomy appliances commonly comprise a pouch for collecting stomal output and are commonly attached to the body by means of a wafer, often via at least one adhesive layer on the wafer. The wafer extends around the stoma of the ostomate. In a "two-piece appliance" a coupling assembly is provided to enable the wafer to be releasably attached to the pouch. A two-piece appliance permits the wafer to be separated from the pouch without damage, so that at least one of the components continues to be functionally usable. For example, the wafer may remain in place on the body of the ostomate whilst the pouch may be replaced.

EP-A-2726033 discloses a coupling for an ostomy appliance. The coupling comprises a substantially non-extendable string functioning as a locking ring in the coupling. The string is twisted by use of a tab when it is moved from an un-locked position to a locked position. The string is provided with a locking element that is able to keep the string in the locked position. The locking element can be provided with a snap-lock so as to keep the clamp ring in the locked or closed position. However, unlocking such a snap-lock is awkward for a user to unlock.

SUMMARY OF THE DISCLOSURE

In this specification, the term "stomal output" refers to any gases or fluids or solids produced by an ostomate that may be secreted from the stoma or that exit the stoma. The stomal output may comprise stomal gas, stomal liquid and stomal solids.

In this specification, the term "stoma" refers to an opening in the body. Generally the stoma is a surgical opening in the torso of the body. In some instances, the term "stoma" also refers to internal tissue, organs or portions thereof that are exposed by the opening. By way of non-limiting example, internal tissue may be selected from colon, ileum, small intestine, large intestine, jejunum, and duodenum, and combinations thereof. The internal tissue may be an end or a loop of a small or large intestine.

In this specification, the term "ostomate" refers to a subject that may have use of the belt mount for an ostomy appliance disclosed herein. While ostomate usually refers to a subject with a surgical opening, as used herein, "ostomate" may refer to a subject who has a stoma, regardless of whether the stoma was created by surgery or other means. The term "user" may refer to an ostomate, or to another person assisting the ostomate, for example, with emptying of the stomal output from the cavity.

In this specification, the ostomy appliances disclosed herein may, for example, be used for managing a stoma created by an esophagostomy, a gastrostomy, a cholecystostomy, a choledochostomy, a cecostomy, a colostomy, a duodenostomy, an ileostomy, a jejunostomy, an appendicostomy, a tracheostomy, a urostomy, a nephrostomy, an ureterostomy, or a vesicostomy. The ostomy appliances disclosed herein may be used with additional devices including, but not limited to, a shunt, a catheter, a plug or a fecal management system.

In this specification locations and orientations of features may be described with reference to the belt mount for an ostomy appliance being "in use", "orientated as it would be in use" or similar. Such terms refer to the intended orientation of the belt mount for an ostomy appliance when it is secured to a body of an ostomate with the ostomate in a standing position, irrespective of whether the ostomy appliance is currently performing such a use or the actual position of the ostomate. In particular, the terms "top" and "bottom" may refer to those locations of the ostomy appliance or the components thereof when in use.

In this specification, the wafer may be for attachment to the body of ostomate around a stoma for attaching the ostomy appliance to the ostomate. The term "wafer" may be used interchangeably with the terms "adapter," "ostomy wafer," "baseplate", or "layered adhesive wafer". The wafer may comprise at least one adhesive layer on a body-facing side for adhering the wafer to the body of the ostomate. A release liner may cover a body-facing side of the wafer that is removed by the user prior to fitting to the skin. The wafer may comprise additional features such as a belt mount.

In this specification, the term "pouch" may be used interchangeably with the term "bag" and may comprise at least one film defining a cavity for collecting stomal output. The pouch may comprise at least one filter for separating stomal solids from stomal liquid and/or gas. The pouch may comprise at least one drain for selectively draining the stomal output from the pouch.

The present disclosure provides a coupling assembly for an ostomy appliance comprising a clamp arrangement, a first coupling and a second coupling, wherein the clamp arrangement comprises: a clamp ring, mounted to the first and/or second coupling, comprising an inner circumference adjustable between clamped and unclamped configurations, wherein in the clamped configuration the clamp ring is for maintaining the first and second couplings in a coupled configuration; and a clamp lock mounted to the clamp ring and adjustable into a locked configuration to lock the clamp ring in the clamped configuration, wherein the clamp lock comprises a clamp actuator moveable radially relative to the inner circumference to unlock the clamp lock from the locked configuration.

It has been realised that the snap-lock of EP-A-2726033 is awkward to unlock because it requires pinching of the snap-lock along the axial direction and therefore a user's fingers must be located in the small, if any, space between the snap-lock and the ostomate's body. The present disclosure avoids such awkward use by allowing unlocking by radial movement of the clamp actuator. A user therefore does not need to located their fingers between the clamp lock and ostomate's body and can simply press the clamp actuator radially with a single finger or thumb.

The clamp actuator may be moveable radially inwardly towards the inner circumference to unlock the clamp lock. The clamp lock may be mounted to and extend radially outwardly from the clamp ring. The clamp lock may comprise a snap-fit mechanism.

The clamp lock may comprise a latch. The latch may comprise a lever engageable with a catch. The clamp actuator may be configured to disengage the lever from the catch when moved radially relative to the inner circumference to unlock the clamp lock from the locked configuration. The clamp actuator may be mounted to the lever. The catch may comprise a hoop and the lever may comprise a hook configured to engage with the hoop in the locked configuration. The lever may be resiliently biased to engage the catch when the clamp ring is in the clamped configuration.

The coupling assembly may further comprise first and second tabs mounted to and extending radially outwardly from the clamp ring. The first and second tabs may comprise the clamp lock. The lever may extend from the first tab and the second tab may comprise the catch. The first and second tabs may be positioned about the clamp ring to be moveable towards one another to reduce the inner circumference and adjust the clamp ring from the unclamped configuration to the clamped configuration.

The inner circumference of the clamp ring may be greater in the unclamped configuration than in the clamped configuration. The clamp ring may be springy and resiliently biased to return from the clamped configuration to the unclamped configuration. The clamp ring may comprise first and second clamp ring ends moveable relative to one another between the clamped and unclamped configurations. The clamp ring may be split.

The second coupling may be configured to be mounted within the first coupling in the clamped configuration. The second coupling may be press-fitted to the first coupling in the clamped configuration.

The first and second couplings may be for mounting to a pouch and a wafer of the ostomy appliance respectively or vice-versa. The present disclosure therefore further provides an ostomy appliance comprising the aforementioned coupling assembly, a pouch and a wafer, wherein the first coupling is attached to the pouch and the second coupling is attached to the wafer or vice-versa such that the wafer and pouch can be disconnected by uncoupling the first and second couplings.

BRIEF DESCRIPTION OF THE DRAWINGS

One or more embodiments of the disclosure will now be described, by way of example only, with reference to the accompanying drawings in which.

DETAILED DESCRIPTION OF THE DISCLOSURE

Figure 1:
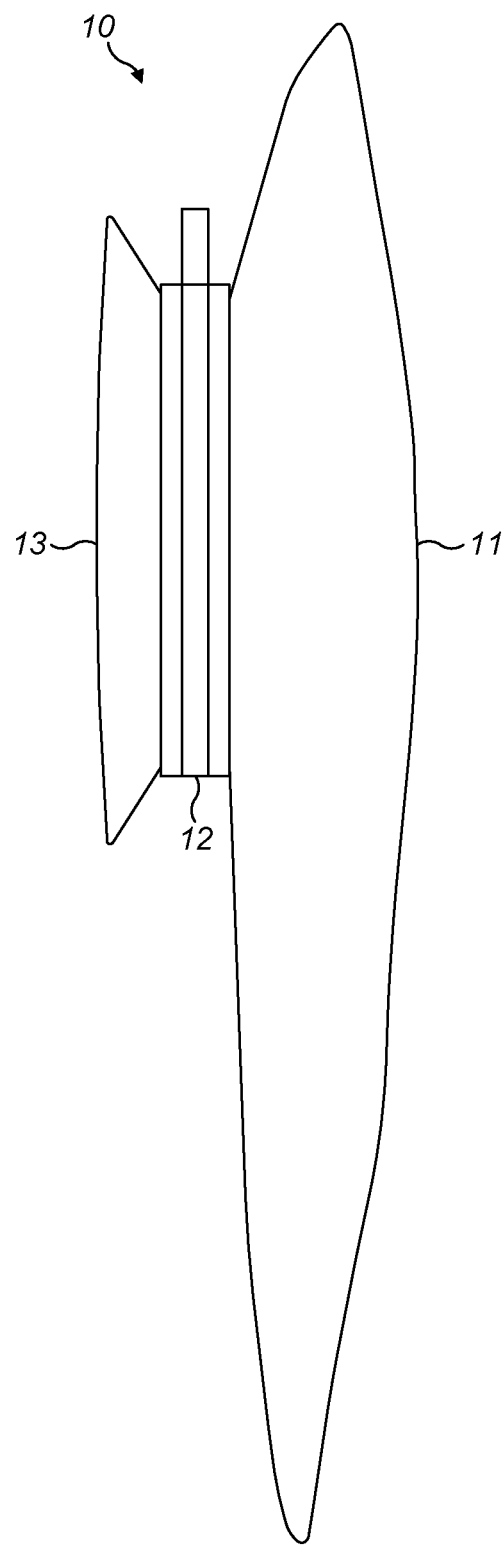
FIG. 1 is a schematic side view of an embodiment of an ostomy appliance comprising a coupling assembly in accordance with the present disclosure.

In the following description, the equivalent reference numerals are used in different embodiments to denote equivalent or similar features. Unless defined otherwise, all technical and scientific terms used in this specification have the same meaning as is commonly understood by the reader skilled in the art to which the claimed subject matter belongs. It is to be understood that the foregoing summary of the disclosure and the following examples are exemplary and explanatory only and are not restrictive of any subject matter claimed.

The following description is directed to embodiments of the disclosure. The description of the embodiments is not meant to include all the possible embodiments of the disclosure that are claimed in the appended claims. Many modifications, improvements and equivalents which are not explicitly recited in the following embodiments may fall within the scope of the appended claims. Features described as part of one embodiment may be combined with features of one or more other embodiments unless the context clearly requires otherwise.

It is to be understood that at least some of the figures and descriptions of the disclosure have been simplified to focus on elements that are relevant for a clear understanding of the disclosure, while eliminating, for purposes of clarity, other elements that the reader skilled in the art will appreciate may also be required. Because such elements are well known to the reader skilled in the art, and because they do not necessarily facilitate a better understanding of the disclosure, a description of such elements is not provided herein.

In this specification, the use of the singular includes the plural unless the context clearly dictates otherwise. In this application, the use of "or" means "and/or" unless stated otherwise.

FIG. 1 illustrates an ostomy appliance 10 in accordance with the present disclosure comprising a pouch 11 for receiving and storing stomal output and releasably attached by a coupling assembly 12 to a wafer 13. The ostomy appliance 10 of the present disclosure may be a two-piece appliance.

Figure 2:
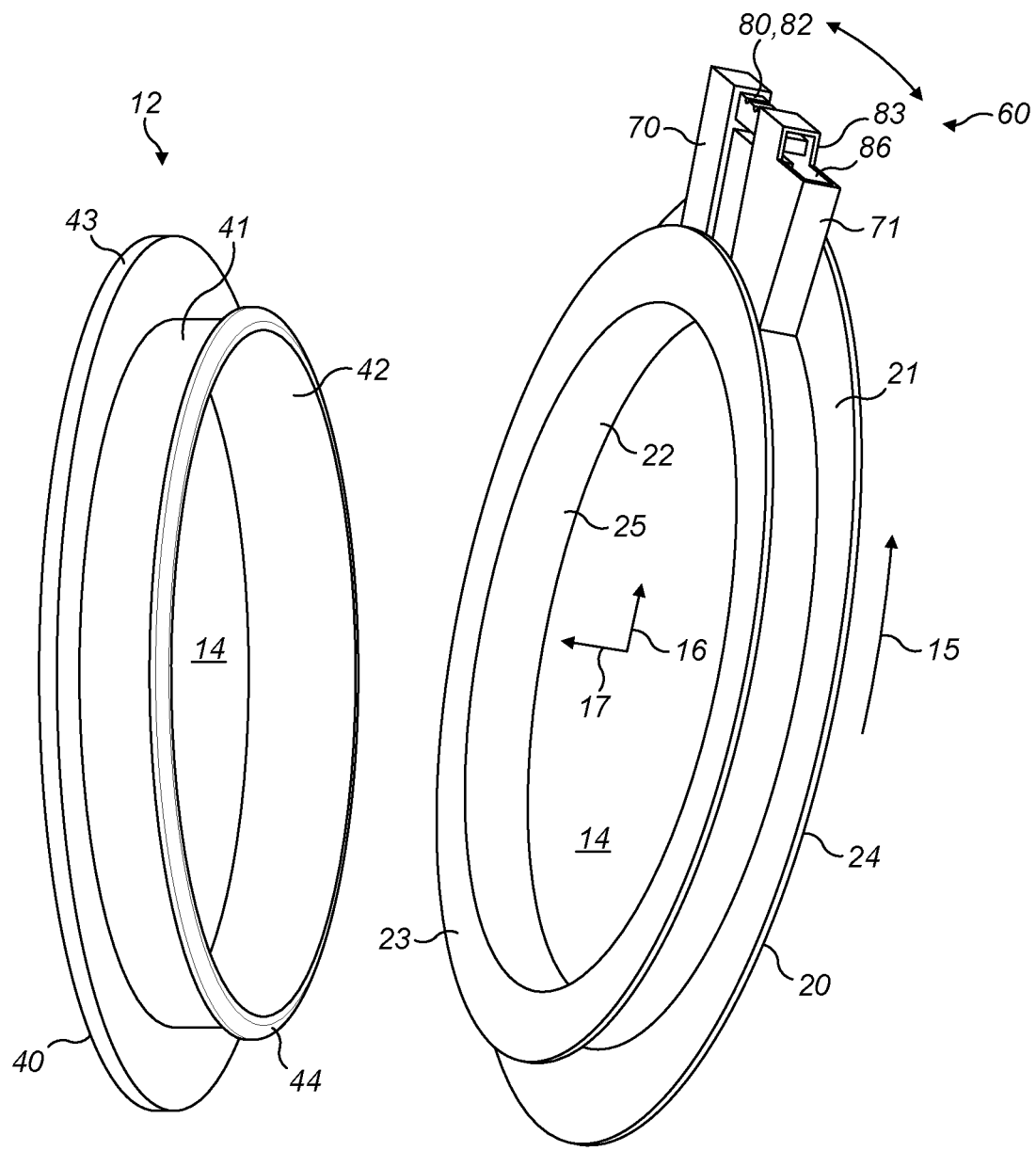
FIG. 2 is a perspective view of the coupling assembly of FIG. 1 in an uncoupled and unclamped configuration.
Figure 3:
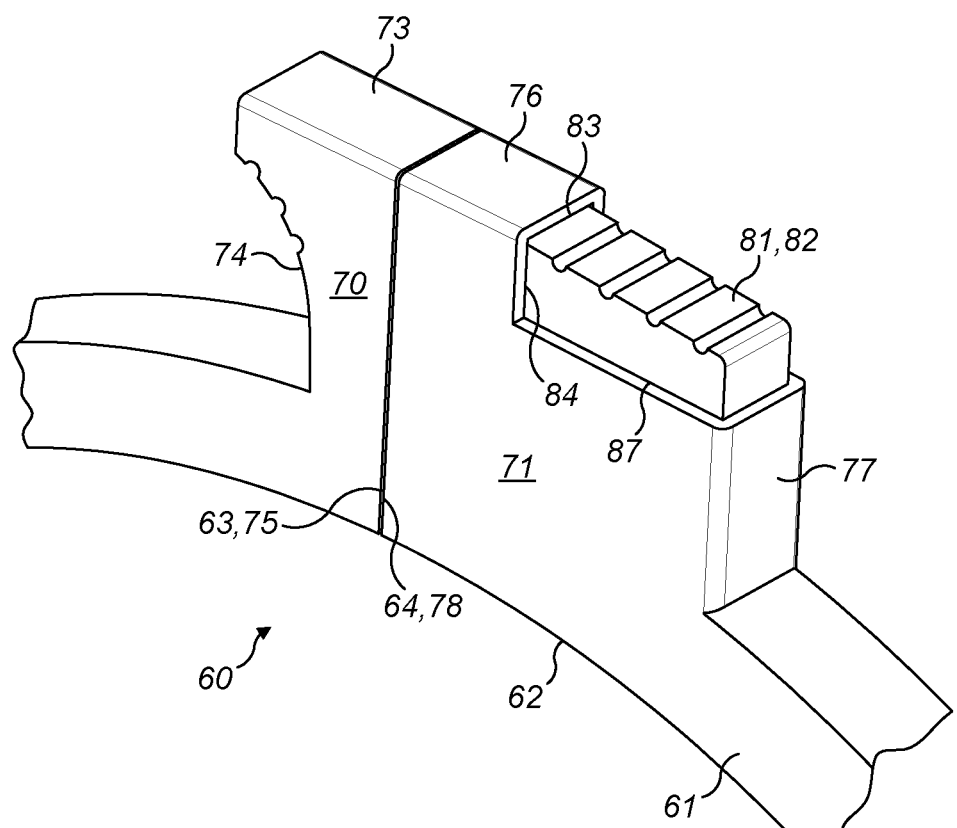
FIG. 3 is a perspective view of a portion of a clamp arrangement of the coupling assembly of FIG. 1 in a clamped configuration.
Figure 4:
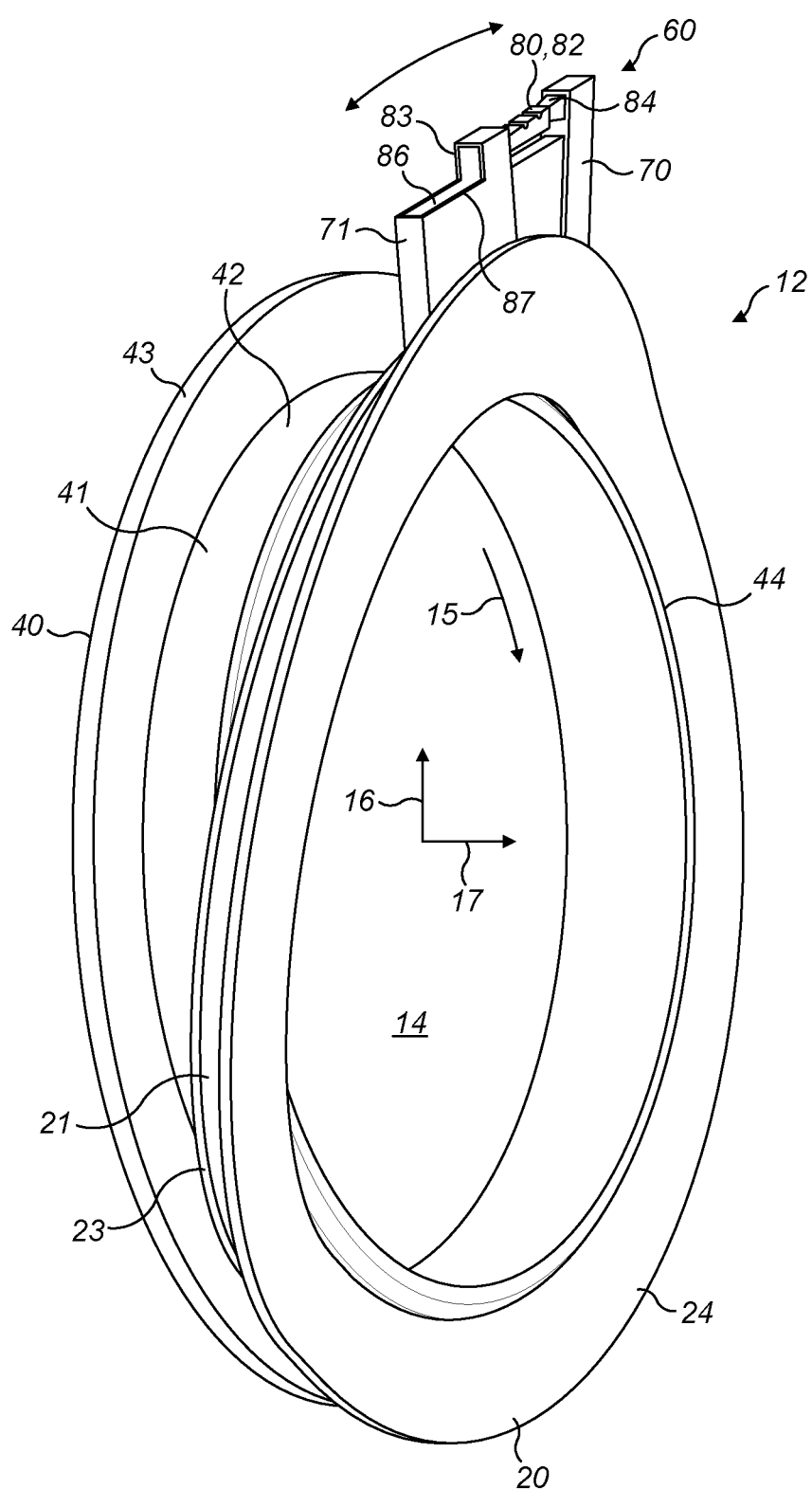
FIG. 4 is a perspective exploded view of the coupling assembly of FIG. 1 in an unclamped configuration and a partially clamped configuration.

As further illustrated in FIGS. 2 to 5, the coupling assembly 12 comprises a first coupling 20, a second coupling 40 and a clamp arrangement 60, which may be moveable relative to one another. The coupling assembly 12 is configurable between a coupled configuration (a partially coupled configuration is illustrated in FIG. 4) and an uncoupled configuration (as illustrated in FIG. 2). In the coupled configuration the ostomy appliance 10 is suitable for use on the ostomate by collecting stomal output and the first and second couplings 20, 40 are coupled or mounted together. In the uncoupled configuration the first and second couplings 20, 40 are uncoupled or separated from each other such that the wafer 13 and/or pouch 11 can be replaced.

In the following example the pouch 11 is mounted to the first coupling 20 and the wafer 13 is mounted to the second coupling 40. The first and second couplings 20, 40 may be uncoupled to separate the pouch 11 from the wafer 13, such as if the pouch 11 is replaced whilst the wafer 13 remains attached to the ostomate's body. However, in other embodiments the pouch 11 may instead be mounted to the second coupling 40 and the wafer 13 may be mounted to the first coupling 20. Additional elements may be mounted between the pouch 11, wafer 13 and first and/or second coupling 20, 40, but generally the uncoupling of the first and second couplings 20, 40 results in the pouch 11 being disconnected and separated from the wafer 13.

The first coupling 20 and second coupling 40 may extend around and define a coupling aperture 14, which may be for stomal output to pass through. The stomal output may therefore pass from the stoma, through a wafer aperture (not illustrated), through the coupling aperture 14, through a pouch aperture (not illustrated) and into the pouch 11.

The coupling assembly 12, first coupling 20, second coupling 40 and/or clamp arrangement 60 may be substantially annular and/or may comprise open or closed rings. The coupling assembly 12, first coupling 20, second coupling 40 and/or clamp arrangement 60 may comprise substantially circular annuli as illustrated, although the annuli may have another elliptical shape, such as oval or the like, or a polygonal shape, such as octagonal or the like.

Components of the present disclosure, particularly the coupling assembly 12, first coupling 20, second coupling 40 and/or clamp arrangement 60, may extend:

circumferentially around the coupling aperture 14, which may be a circumferential direction 15 around the outer perimeter of the coupling aperture 14 and stoma;

radially from the coupling aperture 14, which may be an outward radial direction 16 from the centre of the coupling aperture 14 and stoma, which may be substantially along the ostomate's body; and/or axially, which may be an axial direction 17 through the coupling aperture 14 perpendicular to the circumferential and radial directions.

Components of the present disclosure, particularly the coupling assembly 12, first coupling 20, second coupling 40 and/or clamp arrangement 60, may have:

a length, which may be their dimension in the circumferential direction 15 around the coupling aperture 14;

an outer width, which may be their maximum outer dimension in the radial direction 16;

a breadth, which may be their dimension in the radial direction 16 from their inner perimeter 25 to their outer perimeter (i.e. the breadth of the annulus); and/or a thickness, which may be their dimension in the axial direction 17.

The second coupling 40 may be configured to be mounted within an inner perimeter 25 of the first coupling 20 in the clamped configuration. Thus the second coupling 40 may form and be exposed to the coupling aperture 14, but not the first coupling 20 and/or clamp arrangement 60. The second coupling 40 may be mounted to the first coupling 20 by being press-fitted therein in the clamped configuration. The first and second couplings 20, 40 may comprise annuli having substantially U-shaped cross-sections configured to mate with one another in the clamped configuration. In particular, the first coupling 20 may be mounted at least partially inside a second coupling channel 41 of the second coupling 40.

Figure 5:
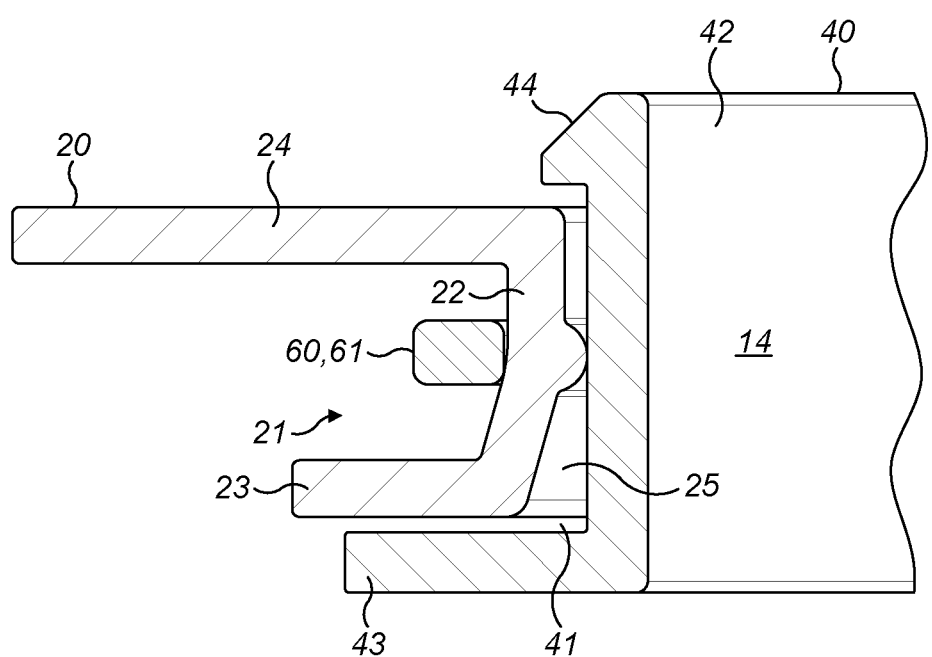
FIG. 5 is a cross-sectional side view across the breadth of the coupling assembly of FIG. 1.

The first coupling 20 is illustrated in further detail in FIGS. 2, 4 and 5 and may comprise a first coupling channel 21, which may face radially outwardly from the coupling aperture 14 and may be configured to receive at least part of the clamp arrangement 60 in the coupled configuration. The first coupling 20 may comprise a first coupling wall 22, which may extend axially such that its thickness is greater than its depth. The first coupling 20 may comprise first coupling inner and/or outer flanges 23, 24, which may extend radially outwardly from the opposing axial edges of the first coupling wall 22. The first coupling outer flange 24 may have a greater breadth than the first coupling inner flange 23. The first coupling wall, inner flange and/or outer flange 22, 23, 24 may form the first coupling channel 21 and the first coupling 20 may have a substantially U-shaped cross-section (i.e. across its breadth). The pouch 11 or wafer 13 may be mounted to the first coupling outer flange 24.

The second coupling 40 is illustrated in further detail in FIGS. 2, 4 and 5 and may comprise a second coupling channel 41, which may face radially outwardly from the coupling aperture 14 and may be configured to receive at least part of the first coupling 20 in the coupled configuration. The second coupling 40 may comprise a second coupling wall 42, which may extend axially such that its thickness is greater than its depth. The second coupling 40 may comprise second coupling inner and/or outer flanges 43, 44, which may extend radially outwardly from the opposing axial edges of the second coupling wall 42. The second coupling inner flange 43 may have a greater breadth than the second coupling outer flange 44. The second coupling wall, inner flange and/or outer flange 42, 43, 44 may form second coupling channel 41 and the second coupling 40 may have a substantially U-shaped cross-section (i.e. across its breadth). The pouch 11 or wafer 13 may be mounted to the second coupling inner flange 43.

FIGS. 2, 4 and 5 illustrated the transition of the coupling assembly 12 from the uncoupled configuration (FIG. 2), through a partially coupled configuration (FIG. 4) and to the coupled configuration (FIG. 5). During coupling the second coupling 40 may be mounted inside an inner perimeter 25 of the first coupling 20 and, in particular, the first coupling 20 may be partially mounted into the second coupling channel 41. The second coupling outer flange 44 may be chamfered to help guide the first coupling 20 around it and into the second coupling channel 41. In the coupling configuration the first and second coupling walls 22, 42 may be adjacent to and/or abut one another, the first and second coupling inner flanges 23, 43 may be adjacent to and/or abut one another and/or the first and second coupling outer flanges 24, 44 may be adjacent to and/or abut one another.

At least part of the first and second couplings 20, 40 may be resiliently deformable and flexible to allow the second coupling 40 to be inserted and removed through the inner perimeter 25 of the first coupling 20. For example, at least the second coupling outer flange 44 may be resiliently deformable. Such resilient deformability may assist in forming the press-fit and may also result in a seal between the first and second coupling 20, 40. Alternatively at least one separate sealing element may be provided between the first and second coupling 20, 40 to form a seal therebetween.

It will be appreciated that any other configuration of the first and second coupling 20, 40 may be implemented provided that they can be moved between the coupled and uncoupled configuration and that they can be clamped together by the clamp arrangement 60 in the coupled configuration.

The clamp arrangement 60 is for clamping the first and second couplings 20, 40 together in the coupled configuration. As illustrated in further detail in FIGS. 3 to 5, the clamp arrangement 60 comprises a clamp ring 61 mounted around and to the first and/or second coupling 20, 40. In particular, the clamp ring 61 may be mounted to the first coupling 40 and may be mounted in and extend around its first coupling channel 21. The clamp ring 61 may be annular and extend circumferentially as illustrated.

The clamp ring 61 has an inner circumference 62 and is adjustable between a clamped configuration (illustrated in FIG. 3) and an unclamped configuration (illustrated in FIG. 3). In the clamped configuration the clamp ring 61 maintains the coupling assembly 12 in the coupled configuration, preferably by holding and/or compressing the first and second coupling 20, 40 together, and the inner circumference 62 of the clamp ring 61 may be less than in the unclamped configuration. In the unclamped configuration the clamp ring 61 allows the coupling assembly 12 to be adjusted to the uncoupled configuration, particularly by allowing separation of the first and second coupling 20, 40.

The clamp ring 61 may be springy, preferably in at least the radial direction 16, and may be resiliently biased to reduce the inner circumference 62 and return from the unclamped configuration to the clamped configuration. As in the illustrated embodiment the clamp ring 61 may be flexible and substantially non-extendable along its length. The inner circumference 62 may be adjustable by virtue of the clamp ring 61 comprising first and second clamp ring ends 63, 64 moveable relative to one another between the locked and unclamped configurations. The clamp ring 61 may be split such that the first and second clamp ring ends 63, 64 are free ends. The first and second clamp ring ends 63, 64 may abut each other when in the clamped configuration. In the illustrated embodiment, the clamp ring 61 includes a continuous member that defines an annulus, and which extends between and connects the first and second clamp ring ends 63, 64.

The clamp arrangement 60 may further comprise first and second tabs 70, 71 extending, preferably radially outwardly, from the clamp ring 61 for adjusting the inner circumference 62. The first and second tabs 70, 71 may be positioned about the clamp ring 61 to be moveable towards one another to reduce the inner circumference 62 and adjust the clamp ring 61 from the unclamped configuration to the clamped configuration. Such adjustment or movement may be initiated by the user pinching the first and second tabs 70, 71 together.

The clamp ring 61 may be resiliently biased to move the first and second tabs 70, 71 away from each other such that the clamp ring 61 is adjusted from the clamped configuration to the unclamped configuration. In particular, the user may not need to apply a force to allow them to move apart and can simply release them.

The first and second tabs 70, 71 may be located at the top of, or at least in the top half of, the coupling assembly 12 and ostomy appliance 10 when in use such that they are easily accessible. The first tab 70 may extend radially from the clamp ring 61 to a first tab outer end 73 and may extend circumferentially around the clamp ring 61 between first tab distal and proximal ends 74, 75. The second tab 71 may extend radially from the clamp ring 61 to a second tab outer end 76 and may extend circumferentially around the clamp ring 61 between second tab distal and proximal ends 77, 78. The first and second tab proximal ends 75, 78 may form the first and second clamp ring ends 63, 64 and may abut each other when in the clamped configuration. As illustrated in FIG. 3, the first tab distal end 74 may be hooked to allow a user's finger or thumb to fit under it and grip it during pinching.

The clamp arrangement 60 comprises a clamp lock 80 mounted to the clamp ring 61 and adjustable into a locked configuration to lock the clamp ring 61 in the clamped configuration. The clamp lock 80 may be mounted to and extend radially outwardly from the clamp ring 61.

The clamp lock 80 comprises a clamp actuator 81 moveable radially relative to (i.e. inwardly to or outwardly from and along the radial direction 16) the inner circumference 62 to unlock the clamp lock 80 from the clamped configuration. The clamp actuator 81 may be moveable radially inwardly along the radial direction 16 towards the inner circumference 62 to unlock the clamp lock 80. The clamp lock 80 may be located at the top of, or at least in the top half of, the coupling assembly 12 and ostomy appliance 10 when in use such that they are easily accessible.

The clamp lock 80 may comprise a snap-fit mechanism, which may be a cantilever snap-fit mechanism, and/or a latch. The latch may comprise a lever 82 engageable with a catch 83. The clamp actuator 81 may be configured to disengage the lever 82 from the catch 83 when moved radially relative to the inner circumference 62, which may subsequently unlock the clamp lock 80 from the locked configuration. The lever 82 may be resiliently biased to engage the catch 83 when the clamp ring 61 is in the clamped configuration. The clamp actuator 81 may be mounted to the lever 82 and thus may form part of the lever 82 as illustrated. The clamp actuator 81 may comprise a grip portion, which may comprise a plurality of indentations, of the lever 82 as illustrated. Furthermore, as illustrated, the catch 83 comprises a hoop and the lever 82 comprises a hook 84 configured to engage with the hoop in the clamped configuration.

The first and second tabs 70, 71 may comprise the clamp lock 80 as illustrated, although in other embodiments additional tabs or the like may be provided for pinching by the user to clamp the clamp arrangement 60. In particular, clamp lock 80 may be in the locked configuration when the first and second tabs 70, 71 abut one another (as in FIG. 3) and may be in the unlocked configuration when the first and second tabs 70, 71 are separated from one another (as in FIGS. 2 and 4).

The lever 82 may extend circumferentially from the first tab 70 and may extend from the first tab proximal end 75, preferably adjacent to the first tab outer end 73. The lever 82 may extend to the hook 84, which may comprise an outwardly projecting wall against which the catch 83 may abut in the locked configuration. The lever 82 may then extend from the hook 84 through the clamp actuator 81 to the free end of the lever 82.

The second tab 71 may comprise the catch 83, which may be in the form of a hoop as illustrated for the hook 84 to hook around in the locked configuration. The second tab 71 may comprise a second tab recess 86 in the second tab distal end 78 and the second tab recess 86 may extend to a second tab opening 87 at the second tab outer end 76. The catch 83 may be formed at an edge of the second tab opening 87. In the locked configuration the lever 82 may extend through the second tab recess 86 and be exposed at the second tab opening 87. In particular, the clamp actuator 81 may be exposed at the second tab opening 87 and the outwardly projecting wall of the hook 84 may abut the second tab opening 87 to lock the lever 82 in place.

In the unlocked configuration the lever 82 may be only partially, or not at all, in the second tab recess 86. During locking the first and second tabs 70, 71 may be pinched towards one another. The lever 82 may be inserted into and travel through the second tab recess 86. The clamp actuator 81 may slide under the catch 83 until the lever 82 has travelled sufficiently far for the hook 84 to reach the catch 83, at which point the lever 82 springs radially outwardly such that the hook 84 moves radially outwardly to hook around the catch 83. The engagement between the lever 82, particularly the hook 84 thereof, and catch 83 may maintain the clamp arrangement 60 in the locked configuration.

During unlocking the clamp actuator 81 may be pressed radially inwardly and downwardly such that the hook 84 is pushed down under the catch 83. The clamp ring 61 may be resiliently biased to spring apart back into the unlocked configuration.

The first coupling 20, second coupling 40 and clamp arrangement 60 may be formed by moulding each component separately and then assembling them together. The first and second couplings 20, 40 may be resiliently deformable as discussed above and the clamp arrangement 60 may be more rigid than the first and second couplings 20, 40.

The first coupling 20, second coupling 40 and/or clamp arrangement 60 may comprise at least one of polyethylene (PE), low density PE (LDPE), high density PE (HDPE), polypropylene homopolymer (PP-H), acrylonitrile butadiene styrene (ABS), an ethylene based octene plastomer (such as Exact® 0230), polypropylene (PP, such asSabic® 58MNK 10), thermoplastic material and the like. In an embodiment the first and second couplings 20, 40 may comprise PE, such as LDPE, and/or the clamp arrangement 60 may comprise PP-H or ABS.

Various alternatives to the embodiments discussed above also fall within the scope of the present disclosure. The clamp ring 61 may be elasticated or comprise a cable or the like. The clamp ring 61 may not be split and instead a flexible joint, catch or the like may be provided between the first and second clamp ring ends 63, 64.

The invention claimed is:

1. A coupling assembly for an ostomy appliance, the coupling assembly comprising:
 a clamp arrangement, a first coupling and a second coupling, wherein the clamp arrangement comprises:
 a clamp ring, mounted to the first and/or second coupling, comprising an inner circumference adjustable between clamped and unclamped configurations, wherein in the clamped configuration the clamp ring is for maintaining the first and second couplings in a coupled configuration, and wherein the clamp ring comprises a continuous member defining an annulus; and
 a clamp lock mounted to the clamp ring and adjustable into a locked configuration to lock the clamp ring in the clamped configuration, wherein the clamp lock comprises a clamp actuator moveable radially relative to the inner circumference to unlock the clamp lock from the locked configuration, wherein the clamp actuator is moveable radially to unlock the clamp lock and the clamp lock comprises a latch, wherein the latch comprises a lever engageable with a catch, the clamp actuator being configured to disengage the lever from the catch when moved radially relative to the inner circumference to unlock the clamp lock from the locked configuration.

2. A coupling assembly as claimed in claim 1 wherein the clamp lock is mounted to and extends radially outwardly from the clamp ring.

3. A coupling assembly as claimed in claim 1, wherein the clamp lock comprises a snap-fit mechanism.

4. A coupling assembly as claimed in claim 1, wherein the clamp actuator is mounted to the lever.

5. A coupling assembly as claimed in claim 4 wherein the catch comprises a hoop and the lever comprises a hook configured to engage with the hoop in the locked configuration.

6. A coupling assembly as claimed in claim 4, wherein the lever is resiliently biased to engage the catch when the clamp ring is in the clamped configuration.

7. A coupling assembly as claimed in claim 1, further comprising first and second tabs mounted to and extending radially outwardly from the clamp ring.

8. A coupling assembly as claimed in claim 7 wherein the first and second tabs comprise the clamp lock.

9. A coupling assembly as claimed in claim 8, wherein the lever extends from the first tab and the second tab comprises the catch.

10. A coupling assembly as claimed in claim 7 wherein the first and second tabs are positioned about the clamp ring to be moveable towards one another to reduce the inner circumference and adjust the clamp ring from the unclamped configuration to the clamped configuration.

11. A coupling assembly as claimed in claim 1, wherein:
 the inner circumference of the clamp ring is greater in the unclamped configuration than in the clamped configuration; and/or
 wherein the clamp ring is springy and resiliently biased to return from the clamped configuration to the unclamped configuration; and/or
 wherein the clamp ring comprises first and second clamp ring ends moveable relative to one another between the clamped and unclamped configurations; and/or
 wherein the second coupling is configured to be mounted within the first coupling in the clamped configuration; and/or
 wherein the second coupling is press-fitted to the first coupling in the clamped configuration.

12. A coupling assembly of claim 1, comprising an ostomy appliance comprising a pouch and a wafer, wherein the first coupling is attached to the pouch and the second coupling is attached to the wafer or vice-versa such that the wafer and pouch can be disconnected by uncoupling the first and second couplings.

13. The coupling assembly of claim 1, wherein the clamp ring is split.

14. The coupling assembly of claim 1, wherein the clamp lock is configured to transition from the locked state to the unlocked state in response to radially-inward movement of the lever.

15. A coupling assembly for an ostomy appliance, the coupling assembly comprising:
 an inner coupling;
 an outer coupling mounted about the inner coupling; and
 a clamp arrangement comprising:
 a clamp ring mounted about the outer coupling, wherein the clamp ring comprises a continuous member defining an annulus; and
 a clamp lock having a locked state in which the clamp lock retains the clamp ring in a clamped state and retains engagement between the inner coupling and the outer coupling, and an unlocked state in which the clamp ring is in an unclamped state and permits separation of the inner coupling and the outer coupling;
 wherein the clamp lock comprises a lever configured to transition the clamp lock between the locked state and the unlocked state as the lever moves radially relative to the outer coupling; and
 wherein the clamp ring is rotatable relative to the outer coupling when the clamp ring is in the unclamped state.

16. The coupling assembly of claim 15, wherein the clamp lock is configured to transition from the locked state to the unlocked state in response to radially-inward movement of the lever.

17. The coupling assembly of claim 15, wherein the clamp ring is split.

* * * * *